United States Patent [19]
Cahill et al.

[11] Patent Number: 5,915,269
[45] Date of Patent: Jun. 22, 1999

[54] METHOD AND APPARATUS TO COMPENSATE FOR GAS CHROMATOGRAPH COLUMN PERMEABILITY

[75] Inventors: Jerry E. Cahill, Trumbull; David H. Tracy, Norwalk, both of Conn.

[73] Assignee: The Perkin-Elmer Corporation, Norwalk, Conn.

[21] Appl. No.: 09/059,927

[22] Filed: Apr. 14, 1998

Related U.S. Application Data

[60] Provisional application No. 60/043,550, Apr. 15, 1997.

[51] Int. Cl.$^6$ .......................... B01D 15/08; G06F 15/20; G01N 30/02
[52] U.S. Cl. .............................. 73/23.35; 364/806; 95/15; 95/87; 422/89; 436/161
[58] Field of Search ................................ 73/23.35, 23.36, 73/61.52; 364/806; 436/161; 95/15, 22, 82, 87

[56] References Cited

U.S. PATENT DOCUMENTS

| | | | |
|---|---|---|---|
| 3,500,028 | 3/1970 | Killian | 235/183 |
| 3,501,700 | 3/1970 | Boyd, Jr. | 328/127 |

(List continued on next page.)

OTHER PUBLICATIONS

Vezzani S et al: "Automatic prediction of retention times in multi–linear programmed temperature analyses"—Journal of Chromatography A, vol. 767, No. 1–2, Apr. 11, 1997, pp. 115–125.

Vezzani S et al: "Fast and Accurate Method for the Automatic Prediction of Programmed–Temperature Retention Times"—Journal of Chromatography A, vol. 677, No. 2, Aug. 19, 1994, pp. 331–343.

Jiping C et al: "Novel approach for the Prediction of Retention Times in Operating Parameter Programmed Gas–Liquid Chromatography with Capillary Columns"—Journal of Chromatography A, vol. 795, No. 2, Feb. 6, 1998, pp. 305–317.

(List continued on next page.)

*Primary Examiner*—Hezron Williams
*Assistant Examiner*—J. David Wiggins
*Attorney, Agent, or Firm*—David Aker

[57] ABSTRACT

In a gas chromatograph system having a column with a stationary phase and a carrier gas moving through the column to contact the stationary phase, the system being useful for detecting analytes in a sample, a method and apparatus for predicting the retention times for the analytes under various conditions, the method utilizing the steps of:

a) detecting the analytes under a number of sets of given conditions;

b) calculating values for various parameters characteristic of the system based on a mathematical model that includes a correction to compensate for the permeability of said column to said carrier gas;

c) entering into the model the values for the characteristic parameters and at least one further set of conditions; and d) using the model to predict retention times for conditions other than those of step a;

the apparatus composed of a data handling system including a model for predicting retention times at a variety of conditions of operation of the system, the model having a first set of inputs including retention times determined during a number of operating condition sets; and a second input representative of the permeability of the column to the carrier gas, the data handling system possessing a prediction mechanism for putting into the model a set of conditions other than those of a) above and for putting in the set of parameters, and for predicting retention times for those conditions other than those of a).

48 Claims, 2 Drawing Sheets

U.S. PATENT DOCUMENTS

| | | | |
|---|---|---|---|
| 3,527,926 | 9/1970 | Holy | 235/61.6 |
| 3,585,002 | 6/1971 | Boys | 23/232 |
| 3,722,181 | 3/1973 | Kirkland et al. | 55/67 |
| 3,733,474 | 5/1973 | Edwards et al. | 235/151.35 |
| 3,898,837 | 8/1975 | Boege | 73/23.1 |
| 4,054,432 | 10/1977 | Taylor et al. | 55/386 |
| 4,740,903 | 4/1988 | Nakatsuka et al. | 364/497 |
| 4,824,446 | 4/1989 | Mowery, Jr. | 55/67 |
| 4,835,708 | 5/1989 | Frans | 364/497 |
| 5,121,443 | 6/1992 | Tomlinson | 382/29 |
| 5,163,979 | 11/1992 | Patrick et al. | 55/21 |
| 5,405,432 | 4/1995 | Snyder et al. | 95/82 |
| 5,476,000 | 12/1995 | Henderson et al. | 73/23.27 |
| 5,545,252 | 8/1996 | Hinshaw et al. | 95/15 |
| 5,592,402 | 1/1997 | Beebe et al. | 364/578 |
| 5,670,379 | 9/1997 | Ito et al. | 436/161 |
| 5,719,322 | 2/1998 | Lansbarkis et al. | 73/23.39 |
| 5,827,946 | 10/1998 | Klee et al. | 73/23.36 |

OTHER PUBLICATIONS

Guillaume Y et al: "Prediction of Gas Chromatographic Retention Times, Column Effeciency and Resolution as a Function of Temperature and Flow–Rate Application for Gas Chromatographic Separation of Eight p–hydroxybenzoic Esters"—Journal of Chromatograph A, vol. 704, No. 2, Jun. 9, 1995, pp. 437–447.

METHOD AND APPARATUS TO COMPENSATE FOR GAS CHROMATOGRAPH COLUMN PERMEABILITY

This application claims the benefit of Provisional Application No. 60/043,550 filed Apr. 15, 1997.

FIELD OF THE INVENTION

This invention relates to gas chromatographic instruments and particularly to the prediction of how retention times will change with variations in system operating conditions such as column temperature, carrier gas inlet and outlet pressure, carrier gas flow velocity and column dimensions.

BACKGROUND OF THE INVENTION

Gas chromatography involves physically separating constituents of a sample in a carrier gas, which flows through a column, and measuring the separated constituents. A pulse of the sample is injected into the flow of the carrier gas and the constituents interact with a stationary phase material in a column. At the end of the column the individual components are more or less separated in time. Detection of the carrier with the separated constituents provides a pattern of retention times, which, by calibration or comparison with known samples, indicates the constituents of the sample qualitatively and quantitatively. The main components of such a system are the column, an injector with a mixing chamber for introducing the sample into the carrier, a detector at the outlet end of the column, fluid controls, and a computer for treating and displaying the output of the detector. The display generally shows the height of each peak verses its retention time. An oven generally is used to elevate temperature to maintain the sample in a volatile state, and to improve the discrimination of constituents. A typical gas chromatographic system is disclosed in U.S. Pat. No. 5,476,000

It is often desirable to be able to predict how retention times will change in response to changes in the column temperature and inlet carrier gas pressure. Several cases of this are listed below:

For example, a user of one gas chromatography system may want to utilize a method developed on another system and get retention times the same, or nearly the same, as those obtained on the other system for the same sample constituents. Even when the two gas chromatographs are very accurately calibrated, this has generally not been possible due to differences in column geometry from one column to another of the same type.

Alternatively, a user may want to simulate effects of changes in temperature and pressure in order to optimize their values for achieving satisfactory separation between the retention times of the various possible sample constituents in the minimum analysis time. A means of achieving this is also described in the accompanying patent application. In addition to this invention, there are products on the market which also claim to be able to do this.

Yet another reason for wanting to be able to make such predictions is to transfer a method from one column to another of a different geometry, possibly using a different carrier gas, and get the same retention time pattern. Means for achieving this are described, for example, in U.S. Pat. No. 5,405,432.

Other situations in which it is desirable to be able to predict the effect of changes in pressure on retention times involve changes in column outlet pressure, which is most commonly atmospheric pressure. One of these situations involves naturally occurring fluctuations in atmospheric pressure. Compensation for outlet pressure makes retention times more constant from one run to the next on a given system. U.S. Pat. No. 5,476,000 describes a means for doing this. Another situation is the use of the same method on two different GC systems run at significantly different elevations. Compensation for the differences in atmospheric pressure must be made in order to get the same retention times on the two systems.

Another type of situation involving outlet pressure is the transfer of a method developed with one detector to systems using another detector operated at a different pressure. For example, a method may be developed using a mass spectrometer detector involving a near zero outlet pressure, and then used routinely on systems using detectors with atmospheric outlet pressure. In each of the above cases, it is desirable to be able to accurately calculate the change in operating conditions that will compensate for the change or difference in outlet pressure.

The carrier gas holdup time is the time it takes a small segment of carrier gas to flow from one end of the column to the other. At constant temperature, the constituent retention times are proportional to the carrier gas holdup time. With temperature programming, there is a similar but more complex dependence on the holdup time. Because of this, all of the examples and situations listed above require the ability to accurately predict changes in carrier gas holdup times accompanying changes in column temperature and inlet pressure.

SUMMARY OF THE INVENTION

According to the teachings of this invention there is disclosed herein a method for more accurately predicting retention times for various operating conditions in a gas chromatographic system utilizing the steps of:
a) detecting the analytes under a number of sets of given conditions;
b) calculating values for various parameters characteristic of the system based on a mathematical model that includes the permeability of said column to said carrier gas;
c) entering into the model the values for the characteristic parameters and at least one further set of conditions; and
d) using the model to predict retention times for conditions other than those of step a.

There is further disclosed an apparatus composed of a data handling system including a model for predicting retention times at a variety of conditions of operation of the system, the model having a first set of inputs including retention times determined during a number of operating condition sets; and a second input representative of the permeability of the column to the carrier gas, the data handling system possessing a prediction mechanism for putting into the model a set of conditions other than those of a) above and for putting in the set of parameters, and for predicting retention times for those conditions other than those of a).

The accepted theory for making predictions of the retention time is based on the Poiseuille theory of flow of carrier gas. Through a combination of experimental measurements of carrier gas holdup times and computer simulations, we have deduced that the accepted theory is incomplete, especially in the very common case where the carrier gas is helium and the column is fabricated from fused silica. Correcting the theory is desirable for more accurate application in the examples and situations outlined above.

Furthermore, it is important to be able to calculate the errors accompanying the use of the conventional theory.

What the accepted theory does not take into account is the finite permeability of fused silica, or other column materials, to helium or other carrier gasses, and the variation of this permeability with temperature. By incorporating this phenomenon into the theory, we are able to make more accurate predictions of how the carrier gas holdup times, and thus the retention times of the simple constituents, vary with temperature and pressure. This increased accuracy improves the methods for reducing retention time variations and fluctuations outlined above.

The retention times are related to the system characteristics and operating parameters by a mathematical function including thermodynamic constants associated with interactions of the constituents with the stationary phase of the column. The function relating retention times to those parameters such as temperature and pressure is based on theoretical relationships of a chromatographic system.

DETAILED DESCRIPTION OF THE INVENTION

Figure 1:
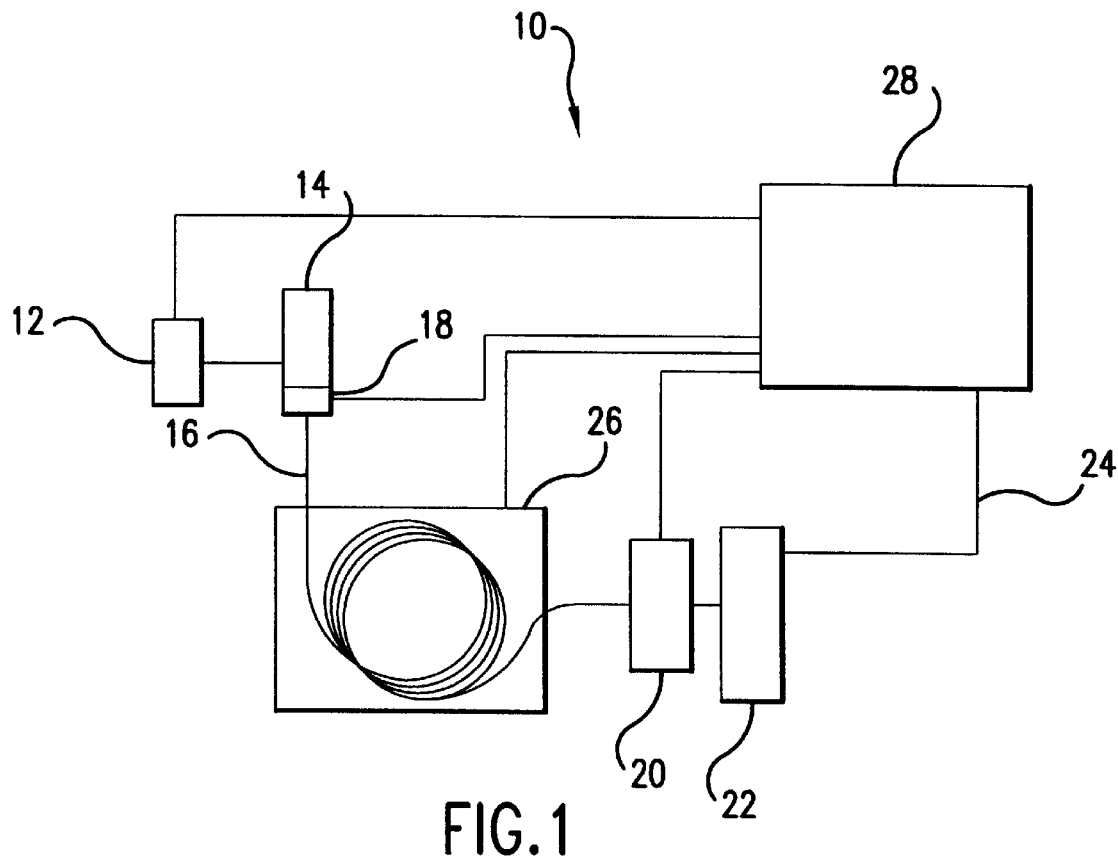
FIG. 1 is a schematic drawing of a chromatographic system incorporating the invention.

The conventional expression for the gas holdup time, the time the carrier remains in the column, is written in different, but equivalent, algebraic forms by different authors. For an example, see G. Guiochon and C. L. Guillemin, "Quantitive Gas Chromatography" (Elsevier, N.Y., 1988), Chapter 2, equations (9) and (17). In U.S. Pat. No. 5,405,432 the holdup time is not expressed directly; instead, it is related to other quantities such as the carrier gas velocity at the column outlet and the James-Martin correction factor for gas compressibilities. A convenient expression for the gas holdup time $t_o$ at constant temperature is $$t_o = \frac{32\eta L^2 (p_i^3 - p_0^3)}{3r^2 (p_i^2 - p_o^2)^2} \quad (1)$$

In this expression, $\eta$ is the carrier gas viscosity at the column temperature, L is the column length, r is the inside radius of the column, $p_i$ is the column inlet pressure and $p_o$ is the column outlet pressure.

Equation (1) is readily derived from Poiseuille's law. It is convenient for our purposes to express this law in a different form given by P. C. Carmen in Flow of Gas Through Porous Media" (Butterworths, London, 1956), p. 62, equation (3.1) as $$u_x p_x = \frac{-r^2}{8\eta} \frac{dp_x^2}{dx} \quad (2)$$

Where x denotes position along the column, $u_x$ is the carrier gas velocity at x averaged across the column, and $p_x$ is the pressure at x. In the standard theory it is assumed that the carrier is an ideal gas and that the carrier mass flow is the same at every point along the column. With these assumptions, the product $u_x p_x$ is a constant independent of x. In this case, equation (2) is readily solved for $p_x$ and $u_x$, and equation (1) for the holdup time is obtained from $$t_0 = \int_0^L u_x^{-1} dx \quad (3)$$

Because of the importance of the gas holdup time in the examples and situations listed above, we have tested the above theory by measuring the helium gas holdup times over a wide range of column dimensions (radius and length), inlet pressure, and temperature. The holdup time was taken to be the retention time for an air sample measured with a thermal conductivity detector. The results were compared with those expected from equation (1) using viscosities for helium as a function of temperature provided by S. J. Hawkes, Chromatographia, 37, 399, 1993.

The measured gas holdup times are expected to vary as the viscosity when the temperature is changed at constant inlet pressure. Deviation from this expected behavior is observed in fused silica columns with helium as the carrier gas. Under most practical combinations of column geometry and operating conditions the deviations are moderate: the gas holdup times typically increase ten percent less than expected. However, with long columns and low carrier gas velocities the deviations can be much greater. In this case, the holdup time increase significantly less rapidly than expected with increasing temperature at moderate temperatures Beyond a critical temperature, the helium flow from the outlet end of the column actually stops.

When gas holdup times are measured as a function of inlet pressure at constant temperature, this phenomenon shows up as deviation from the pressure dependence of the Poiseuille law. As pressure is decreased from a high value, the gas holdup time first rises less rapidly than expected. Below a certain pressure, it rises more rapidly than expected.

We have deduced that the deviations of our experimental results from the conventional theory are due to carrier gas permeating out through the column walls. A study of the literature shows that fused silica, the most common material for GC columns, has a high permeability to helium relative to that of other glasses. This is shown in data published by F. J. Norton, J. Am. Ceram. Soc. 36, 90, 1953. According to Norton the rate of carrier gas permeation through a layer of permeable material can be expressed as $$F=Kp_{cmHg}A_{cm2}/t_{mm} \quad (4)$$

F is the rate of flow through the material in $cm^3$ at standard temperature and pressure (STP), K is the permeation velocity in $cm^3$ gas (STP) mm thickness/s/$cm^2$ area/cm Hg (gas pressure difference). $P_{cmHg}$ is the carrier gas pressure difference across the material in cm Hg, $A_{cm2}$ is the area of the exposed material in $cm^2$ and $t_{mm}$ is the thickness in mm. K is strongly temperature dependent. Its value as a function of temperature can be expressed as:

$$log_{10}K=-6.768-848.1/T-29900T^2 \quad (5)$$

It is convenient for our purposes to use the ideal gas law to express the loss of carrier gas in terms of a change in $p_x$ $u_x$, change the pressure units to Pascals, take into account the cylindrical geometry of the column, and express length in meters and radius in mm. Making these changes we obtain $$d(u_x p_x) = -\frac{2K}{133} \frac{T}{T_S} \frac{p_s p_x}{\ln(r/r_o)} \frac{dx}{r^2} \quad (6)$$

$d(u_x\, p_x)$ is the change in $u_x p_x$ in units of a Pa m/s over a length of dx m. $T_s$ is the normal temperature in K, $P_s$ is the normal pressure in Pa, and $r_o$ is the outer radius of the column.

In order to calculate $u_x$, equations (4) and (5) must be solved simultaneously. These equations are readily integrated numerically using a modern laboratory or office PC. The $u_x$ values thus calculated are then entered into equation (3) to calculate the gas holdup time. In this case, equation (3) cannot be solved in closed form, but must be integrated numerically.

For isothermal chromatography, the modified calculation of carrier gas holdup time is the only change required to calculate retention times. For temperature programming, the situation is not this simple. Retention time $t_R$, for a given constituent of the sample is calculated from the integral equation:

$$\int_0^{t_R} u_x \left(1 + \frac{a}{\beta} e^{b/T+cT}\right)^{-1} dt = L \quad (7)$$

where a, b and c are thermodynamic parameters for the constituent and its interaction with the stationary phase material. $\beta$, the phase ratio of the column, is equal to r/2 d, where d is the thickness of the stationary phase. The carrier gas velocity $u_x$ is a function of temperature, which is in turn a function of time when temperature programming. In solving equation (7), one must keep track of the position x of the constituent as a function of time.

In the conventional theory, the average carrier gas velocity along the column at temperature T, $U_{avg}=L/t_o$, is substituted for $u_x$ in equation (7). The retention times are then calculated from equation (8):

$$\int_0^{t_R} u_{avg} \left(1 + \frac{a}{\beta} e^{b/T+cT}\right)^{-1} dt = L \quad (8)$$

This is easier to solve than equation (7) because u does not depend on x and it is not necessary to keep track of the position of the constituent. Within the framework of the conventional theory this is valid because the pattern of the velocities along the column does not change with temperature. When permeation is taken into account, as described above, the pattern of the velocities does charge with temperature. Because of this equation (7) must be used.

The above does not consider the effects of the stationary phase or the column's polyimide outer coating on the permeation of carrier gas through the column. There are two possible approaches to these layers. One is to assume that their impedance to carrier permeation is negligible compared to the fused silica and thus ignore them. The other is to determine what they are, either through a literature search or experiment, and to include them if necessary.

Another aspect of the invention involves the use of other column materials and coatings to minimize carrier gas permeability. We have experimental data on a very long stainless steel column that indicates that a small, but noticeable, amount of helium permeation is occurring. It is contemplated that an aluminum coating, which is sometimes placed on fused silica columns, would significantly impede carrier gas permeation.

Norton (reference above) shows that many different glasses exhibit significantly less helium permeation than fused silica. It is part of this invention that other less permeable glasses be used to reduce or eliminate carrier gas permeation. One possibility is to fabricate composite columns with an inside surface of fused silica surrounded by a layer of less permeable glass. This would preserve the desirable inside surface properties of fused silica while significantly reducing carrier permeation.

The above invention may be utilized in several ways in the examples and situations outlined in the Background of the Invention. The most straightforward is the use the theory directly as described. This involves using equations (2) and (6) to solve for the $u_x$ values as a function of both x and T, and to use these values to solve equation (7) for thermodynamic properties. These thermodynamic properties are then used to solve equation (7) again to determine standardized retention times for a desired set of conditions. This requires assuming that the nominal geometric parameters of the column, which is all that is generally known, are close enough to the actual for good accuracy. While imperfect, this will produce better accuracy than the conventional theory.

There are also any number of approximate approaches which may be used. For example, with the procedures described above for correctly calculating holdup times, the holdup times for a wide range of situations can be simulated. The results can then be used to deduce a correction to equation (1) along with the range of its validity. This can be used in equation (7) to estimate retention times. While this procedure is only approximate, it has the advantage of requiring only minor modification to existing programs. The invention is utilized in a conventional gas chromatographic system such as described in the above mentioned U.S. Pat. No. 5,476,000.

In FIG. 1, a typical GC system 10 is shown. A carrier gas from a pressure-regulated source 12 is supplied to an injector device 14. A typical carrier gas in a GC system might be argon, helium, hydrogen, methane or nitrogen. A portion of the carrier is passed from the injector 14 into and through a chromatographic column 16. A pressure transducer 18 is connected to measure pressure at the inlet to the column.

A pulse of the sample is injected into the carrier in the injector device where a mixture is formed with the carrier gas. The sample used for characterization may contain organic molecules in combination with chlorine, oxygen, nitrogen or sulphur. The pulsed mixture passes through the column, typically taking several minutes. A stationary phase of a suitable substance on the inside column wall interacts with the chemical constituents of the sample. Different constituents have different affinities for the stationary phase and thereby exit the column at different characteristic retention times. The velocity of the carrier gas contributes to the total retention time.

A second pressure transducer 20 is connected to measure pressure at the outlet of the column. A detector 22 at the column outlet measures a physical property of the carrier and mixture, the magnitude of the property changing with each constituent passing through. Various types of detectors are used, such as hot wire, flame ionization, electron capture, thermionic and flame photometric. The detector effects signals on a line 24, the signals being representative of the retention times. The column 16 is enclosed in an oven 26.

A computer 28 regulates the pressure of carrier gas source 12, receives pressure information from inlet transducer 18, controls the temperature of oven 26, receives pressure information from outlet transducer 20 and also receives and processes the signals on line 28 into a series of peaks representative of the sample constituents, the plotted locations of the components representing corresponding retention times. The inlet pressure is controlled by controlling the pressure of the carrier gas source. The carrier gas source can be controlled by a pressure program which could maintain a constant pressure or cause the pressure to vary. The oven can be controlled by a temperature program which could include an isothermal method or one that varies the temperature by controlling starting and final temperatures, ramp rates and dwell times at each temperature. The column outlet pressure can also be controlled by a pressure program which could maintain a constant pressure or cause the pressure to vary. The carrier gas source, inlet pressure and outlet pressure can also be controlled by a carrier gas flow velocity program which can cause a constant or variable carrier gas flow velocity within the column. The computer displays the retention times directly or other indicators computed from the retention times. The components are then identified by an operator or the computer as known chemical constituents, with the peak heights providing a quantitative measure.

Figure 2:
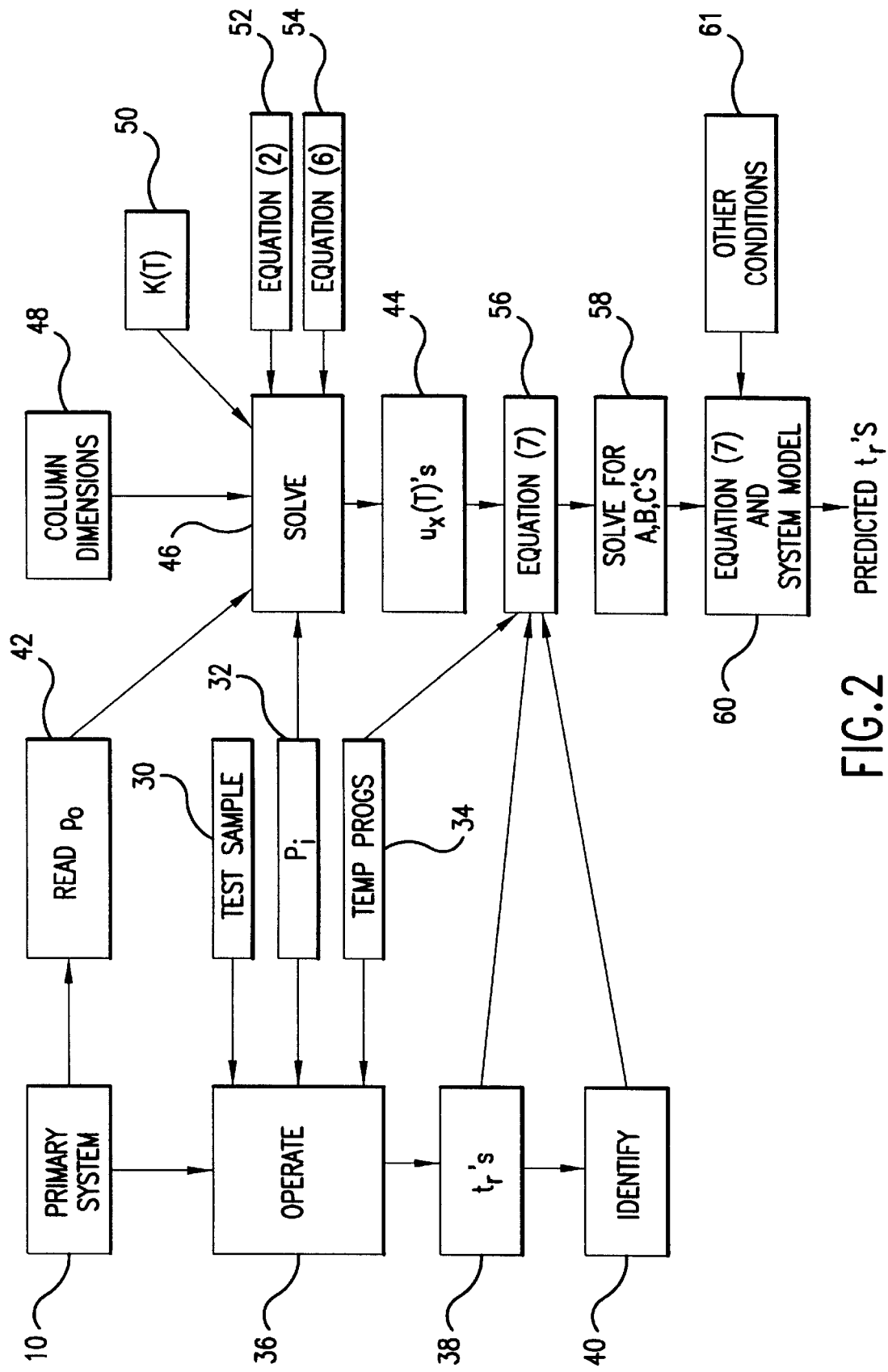
FIG. 2 is a flow chart of an embodiment of the method according to the invention.

FIG. 2 illustrates one embodiment of the method of the invention. Primary system 10 is a typical gas chromatograph as shown in FIG. 1. The first step is to supply the system with a test sample 30 and enter operating parameters including an inlet pressure 32 and various temperature programs 34. The system then operates 36 and generates retention times 38 which are then identified 40 for each constituent of the test sample under each temperature program. Outlet pressure 42 is also read. The next step is to calculate the carrier gas velocities 44 at each of several different distances (x's) along the column at each of several temperatures over the anticipated range of system operating temperatures. We have determined experimentally that the number of positions x, may be a number greater than 200. The result is a two-dimensional array of values. Solving 46 for these velocities requires the column dimensions 48, the permeability 50 of the column material to the carrier gas as a function of pressure, the inlet pressure 32, the outlet pressure 42, as well as equation (2) 52 and equation (6) 54. The velocities 44 along with the temperature programs 34 and the retention time 38 for each sample constituent 40 under each temperature program are entered into equation (7) 56. Equation (7) is solved for each of three different sets of data. The thermodynamic parameters, a, b and c are then calculated 58 for each sample constituent. The thermodynamic constants a and b are related to enthalpy and entropy and are temperature dependent. Thermodynamic constant c is introduced to compensate for this temperature dependency. All of a, b and c are deemed to be constant for each sample constituent but generally are different for different constituents and stationary phases. The thermodynamic constants, a, b and c are then used to solve equation (7) 60 again as part of a model to predict retention times for other operating conditions 61.

Figure 3:
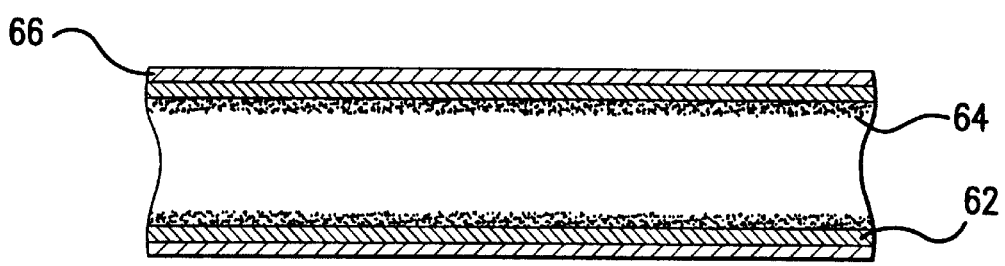
FIG. 3 is a longitudinal section of a portion of a chromatographic column as used in the system of FIG. 1.

FIG. 3 shows the construction of a column. A tube 62 is constructed of fused silica or other suitable material. The appropriate stationary phase 64 is present on the tube's inside surface. A coating 66 is present on the outside surface of the tube to impede permeation of the carrier gas through the tube. The coating layer is only as thick as required to obtain the desired permeation impedance to the carrier gas. Example coating materials are aluminum, glass or stainless steel.

What is claimed is:

1. In a gas chromatograph system having a column with a stationary phase therein, and a carrier gas moving through said column to contact said stationary phase said system being useful for detecting analytes in a fluid sample injected into said system, a method for predicting the retention times for said analytes under various conditions, said method comprising the steps of:
    a) detecting said analytes under a number of sets of given operating conditions;
    b) calculating values for various parameters characteristic of the system based on a mathematical model that includes a correction to compensate for the permeability of said column to said carrier gas;
    c) entering into said model said values for said characteristic parameters and at least one further set of conditions; and
    d) using said model to predict retention times for conditions other than those of step a.

2. The method of claim 1 wherein said sets of given conditions include temperature programs as a function of time for said column.

3. The method of claim 2 wherein said temperature programs are isothermal.

4. The method of claim 2 wherein said temperature programs comprise starting and final temperatures, ramp rates and dwell times at each temperature.

5. The method of claim 1 wherein said sets of given conditions include column inlet pressure programs.

6. The method of claim 5 wherein said column inlet pressure programs maintain constant column inlet pressure.

7. The method of claim 5 wherein said column inlet pressure programs cause column inlet pressure to vary.

8. The method of claim 1 wherein said sets of given conditions include carrier gas flow velocity programs.

9. The method of claim 8 wherein said flow velocity programs maintain constant carrier gas flow velocity.

10. The method of claim 8 wherein said flow velocity programs cause carrier gas flow velocity to vary.

11. The method of claim 1 wherein said sets of given conditions include column outlet pressure programs.

12. The method of claim 11 wherein said column outlet pressure programs maintain constant column outlet pressure.

13. The method of claim 11 wherein said column outlet pressure programs cause column outlet pressure to vary.

14. The method of claim 1 wherein said sets of given conditions include column dimensions.

15. The method of claim 14 wherein said column dimensions include column length, column diameter and thickness of said column stationary phase.

16. The method of claim 1 wherein said various parameters characteristic of the system include thermodynamic characteristics.

17. The method of claim 16 wherein said thermodynamic characteristics include factors for entropy and enthalpy of said carrier gas and a factor to account for changes in said entropy and enthalpy related to temperature.

18. The method of claim 1 wherein said at least one further set of conditions includes temperature programs for said column.

19. The method of claim 18 wherein said temperature programs are isothermal.

20. The method of claim 18 wherein said temperature programs comprise starting and final temperatures, ramp rates and dwell times at each temperature.

21. The method of claim 1 wherein said at least one further set of conditions include column inlet pressure programs.

22. The method of claim 21 wherein said column inlet pressure programs maintain constant column inlet pressure.

23. The method of claim 21 wherein said column inlet pressure programs cause column inlet pressure to vary.

24. The method of claim 1 wherein said at least one further set of conditions include carrier gas flow velocity programs.

25. The method of claim 24 wherein said flow velocity programs maintain constant carrier gas flow velocity.

26. The method of claim 24 wherein said flow velocity programs cause carrier gas flow velocity to vary.

27. The method of claim 1 wherein said at least one further set of conditions include column outlet pressure programs.

28. The method of claim 27 wherein said column outlet pressure programs maintain constant column outlet pressure.

29. The method of claim 27 wherein said column outlet pressure programs cause column outlet pressure to vary.

30. The method of claim 1 wherein said at least one further set of conditions include column dimensions.

31. The method of claim 30 wherein said column dimensions include column length, column diameter and the thickness of said column stationary phase.

32. The method of claim 1 wherein said carrier gas is a gas selected from the group consisting of argon, helium, hydrogen, methane and nitrogen.

33. In a gas chromatograph system including a temperature programmable oven, a column positioned inside said oven having an inlet and an outlet, means for passing carrier gas through said column, means for controlling the pressure at said inlet, means for measuring the pressure at said outlet, injection means for injecting a pulse of sample fluid having constituents into said carrier gas at said inlet to effect a fluid mixture passing through said column having measured retention times for said constituents, detector means receptive of said constituents for effecting signals representative of peak heights verses retention times of said constituents and processing means receptive of said signals for presenting peak heights verses measured retention times, a method for predicting measured retention times under various operating conditions comprising:

specifying a plurality of temperature programs for said oven;

specifying an inlet pressure;

injecting a sample having constituents during each temperature program;

measuring measured retention times of said constituents for each temperature program;

measuring an outlet pressure;

determining dimensions of said column including a column length and a column radium;

determining column permeability to said carrier gas as a function of pressure;

dividing length of said column into a plurality of equal distances;

selecting a plurality of temperatures from said temperature programs;

determining viscosity of said carrier gas at each selected temperature;

calculating carrier gas velocity at points corresponding to each of said plurality of equal distances and at each of said plurality of temperatures as a function of said inlet pressure, said outlet pressure, said column dimensions and said permeability;

calculating thermodynamic parameters of each constituent as a function of said carrier gas velocities, said temperature programs, said retention times, said column dimensions and said viscosities; and calculating retention times as a function of said thermodynamic parameters.

34. The method of claim 33 wherein said carrier gas is a gas selected from the group consisting of argon, helium, hydrogen, methane and nitrogen.

35. The method of claim 33 wherein said plurality of equal distances is greater than 200.

36. The method of claim 33 wherein said thermodynamic parameters are related to entropy and enthalpy of said constituents.

37. The method of claim 33 wherein said column comprises a stationary phase having an effective phase thickness and said column dimensions comprise said phase thickness, column length, and column radius.

38. In a gas chromatograph system having a column; a stationary phase within said column and a carrier gas for carrying a sample containing analytes past said stationary phase, the improvement comprising:

a data handling system including a mathematical model for predicting retention times at a variety of conditions of operation of the system, said model having:

a) first inputs including retention times determined during a number of sets of conditions of operation of said system; and b) a second input representative of a correction to compensate for the permeability of the column to said carrier gas, said data handling system having prediction means for inputting to said model a set of operating conditions other than those of a) and for inputting said set of parameters, and for predicting retention times for said operating conditions other than those of a).

39. The method of claim 38 wherein said numbers of sets of conditions of operation include temperature programs as a function of time for said column.

40. The method of claim 38 wherein said numbers of sets of conditions of operation include column inlet pressure programs.

41. The method of claim 38 wherein said numbers of sets of conditions of operation include carrier gas flow velocity programs.

42. The method of claim 38 wherein said numbers of sets of conditions of operation include column outlet pressure programs.

43. The method of claim 38 wherein said numbers of sets of conditions of operation include column dimensions.

44. The method of claim 38 wherein said conditions other than those of a) includes temperature programs for said column.

45. The method of claim 38 wherein said conditions other than those of a) include column inlet pressure programs.

46. The method of claim 38 wherein said conditions other than those of a) include carrier gas flow velocity programs.

47. The method of claim 38 wherein said conditions other than those of a) include column outlet pressure programs.

48. The method of claim 38 wherein said conditions other than those of a) include column dimensions.

* * * * *